United States Patent
Cook

(10) Patent No.: US 6,258,036 B1
(45) Date of Patent: Jul. 10, 2001

(54) BLOOD PRESSURE INFLATION BULB WITH PERMANENTLY SECURED INTAKE VALVE

(75) Inventor: Daniel G. Cook, Maple Plain, MN (US)

(73) Assignee: Health & Technology, Inc., Plymouth, MN (US)

( * ) Notice: Subject to any disclaimer, the term of this patent is extended or adjusted under 35 U.S.C. 154(b) by 0 days.

(21) Appl. No.: 09/333,061

(22) Filed: Jun. 14, 1999

(51) Int. Cl.[7] .................................................. A61B 5/00
(52) U.S. Cl. ........................ 600/490; 137/150; 417/478
(58) Field of Search ........................... 417/478; 137/150; 600/490, 793–6, 458

(56) References Cited

U.S. PATENT DOCUMENTS

| | | | |
|---|---|---|---|
| 1,269,620 | * | 6/1918 | Levine .................................. 600/499 |
| 1,352,306 | * | 9/1920 | Mott ..................................... 417/478 |
| 2,970,749 | * | 2/1961 | Montague ............................ 417/478 |
| 3,633,567 | * | 1/1972 | Sarnoff ................................. 600/499 |
| 3,906,939 | * | 9/1975 | Aronson ............................... 600/499 |
| 5,098,428 | * | 3/1992 | Sandlin et al. ........................ 606/22 |

* cited by examiner

Primary Examiner—Robert L. Nasser
(74) Attorney, Agent, or Firm—Kinney & Lange, P.A.

(57) ABSTRACT

A hand pump for connection to a pressure control valve used as part of a sphygmomanometer. The hand pump comprising an inflation bulb, a plug and an intake valve. The inflation bulb comprising of an inlet, an outlet and an inner hollow cavity. The outlet of the inflation bulb is connected to the pressure control valve of the sphygmomanometer. The plug is secured at the inlet of the inflation bulb within the inner hollow cavity and the intake valve is secured within the plug.

14 Claims, 3 Drawing Sheets

BLOOD PRESSURE INFLATION BULB WITH PERMANENTLY SECURED INTAKE VALVE

CROSS-REFERENCE TO RELATED APPLICATION(S)

None.

BACKGROUND OF THE INVENTION

The present invention pertains to a hand pump for use with a sphygmomanometer. More particularly, the invention pertains to an inflation bulb with an intake valve permanently secured therein.

Sphygmomanometers are used to measure an individual's blood pressure. A sphygmomanometer includes a hand pump connected to a pressure control valve which is further connected to a pressure cuff through a piece of tubing. The tubing also connects the pressure cuff to a gauge for measuring pressure within the pressure cuff. The pressure control valve includes a thumb screw that acts as a release valve for air at or beyond the pressure control valve within the system.

The sphygmomanometer is used to measure blood pressure by first wrapping the pressure cuff typically around a patient's arm. Next, the pressure cuff is inflated by compressing the hand pump which forces air into the cuff. The thumb screw on the pressure control valve controls the flow of air into or from the pressure cuff. When the thumb screw is closed, air is forced from the hand pump, through the pressure control valve, and into the pressure cuff via the tubing. If the thumb screw is open, the pressure control valve releases air either from within the pressure cuff or as the air is pumped through the pressure control valve by the hand pump.

In order for the hand pump to function properly, it must be compressible and maintain air flow in only one direction. To meet these requirements, the hand pump generally includes an inflation bulb and an intake valve. The inflation bulb is generally constructed out of a rubber type of material which is typically black in color and has an oval shape that includes an inlet and an outlet into the bulb's hollow center. The hollow center of the inflation bulb acts as a reservoir for storing air that will be pumped into the pressure cuff for inflation.

The intake valve is normally inserted into the inlet of the inflation bulb to allow air flow in only one direction. The intake valve is positioned to allow air to flow into the hollow center of the inflation bulb from the surrounding external environment. The intake valve being uni-directional prevents air from exiting the inlet of the inflation bulb once the air is contained within the hollow center. The intake valve operates by allowing air to flow into the inflation bulb when a pressure differential exists across the intake valve at the inlet of the inflation bulb. The pressure differential is created between the hollow center of the inflation bulb and the surrounding external environment. The pressure differential exists when the pressure within the inflation bulb is less than the pressure of the surrounding external environment, such as after the inflation bulb has been compressed. As a result of the pressure differential, the intake valve allows air to flow from the surrounding external environment through the intake valve and into the hollow center of the inflation bulb. This occurs when the inflation bulb is released from a compressed state. Upon equalizing the pressure differential, the intake valve prevents further air flow either into or out of the inlet of the inflation bulb.

Once the center of the inflation bulb is filled with air, the inflation bulb can be compressed to force the air out through the outlet of the inflation bulb, through the pressure control valve, and into the tubing to inflate the pressure cuff. During the compression of the inflation bulb, the intake valve prevents air from escaping through the inlet, thus forcing the air out through the outlet. This cycle is repeated until the pressure cuff is inflated to a desired level.

The appearance of the standard hand pump—primarily the black, rubber, oval shaped inflation bulb—is typically unfamiliar and unappealing to children. When medical personnel attempt to take a child's blood pressure with the standard band pump, it generally creates anxiety in the child. The child's anxiety makes the measurement more difficult and less accurate, which can lead to an increased potential for misdiagnosis. To calm the child's fear and anxiety of the instrument, medical personnel may allow the child to play with the hand pump in the hope that the child may associate with the instrument and overcome their fear. However, the standard hand pump is not safe for young children to handle. In particular, the intake valve at the inlet of the standard type of inflation bulb can be easily removed or unseated. Once removed from the inlet of the inflation bulb, the intake valve is small and creates a choking hazard, especially for young children.

BRIEF SUMMARY OF THE INVENTION

The invention is a hand pump for use with a sphygmomanometer. The hand pump is connected to the sphygmomanometer at a pressure control valve and is used to inflate a pressure cuff. The hand pump is comprised of an inflation bulb, a plug and an intake valve. The inflation bulb has an inner hollow cavity with an inlet and an outlet. The inflation bulb connects to the pressure control valve at the outlet to form part of the sphygmomanometer.

The plug includes a top, a bottom, a radial sidewall and an inner center passage bore from the top of the plug to the bottom. The radial sidewall includes an outward radial extension near the bottom of the plug. The plug is secured to the inflation bulb at the inlet by forming the inflation bulb around the plug. The plug is secured to the inlet of the inflation bulb so that at least a portion of the bottom of the plug is exposed to the surrounding external environment and so that the top of the plug is contained within the inner hollow cavity of the inflation bulb.

The intake valve allows unidirectional air flow from an input end to an output end. The intake valve is secured within the inner center passage bore in the plug. The intake valve is secured within the passage of the plug so that the input end is located at the bottom of the plug and the output end is located at the top of the plug. The passage of the plug is notched to resemble an exterior surface of the intake valve to maintain the intake valve within the plug. The intake valve is thus secured and retained within the plug, which is secured and retained within the inflation bulb.

DETAILED DESCRIPTION

Figure 1:
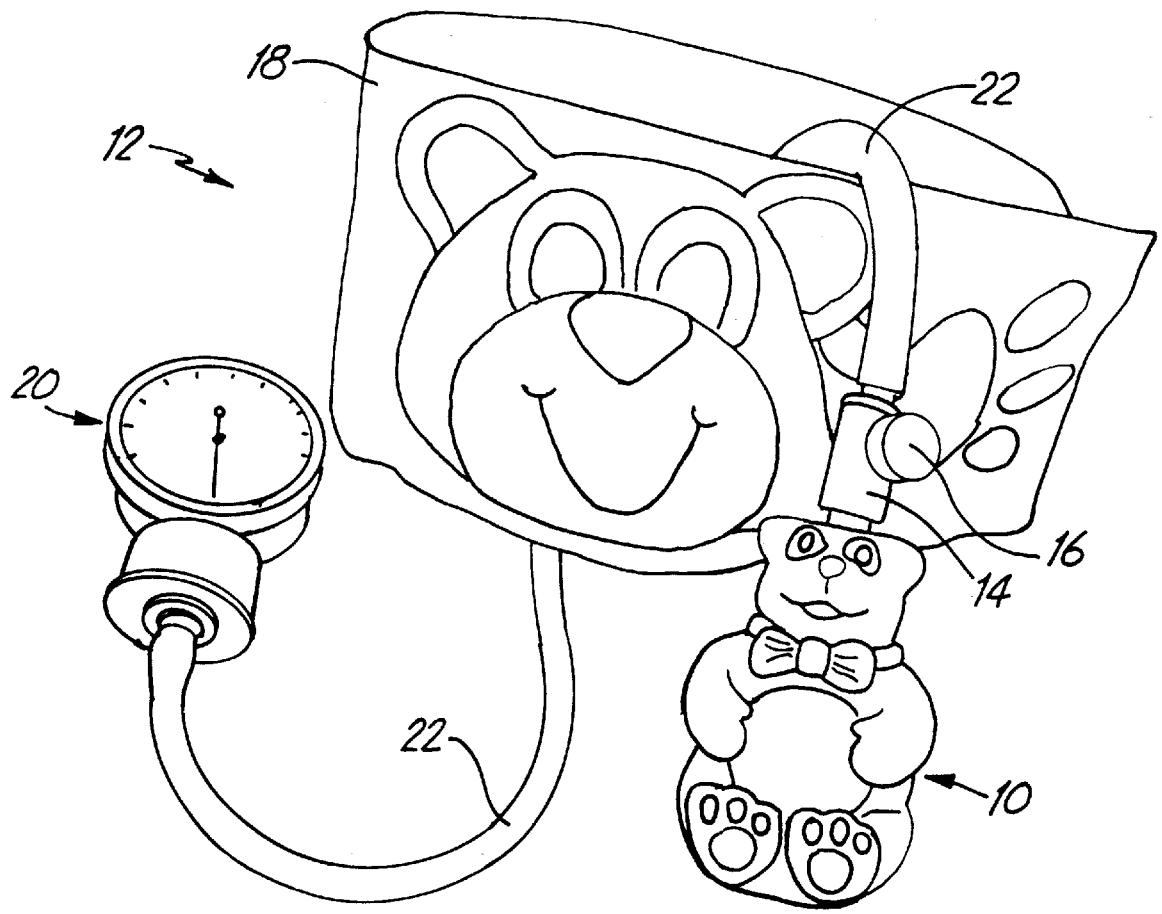
FIG. 1 is perspective view of a preferred embodiment of the invention.

FIG. 1 illustrates a preferred embodiment of a hand pump 10 that is used as part of a sphygmomanometer 12. The sphygmomanometer 12 is used to measure blood pressure and includes, in addition to the hand pump 10, a pressure control valve 14 with a thumb screw 16, a pressure cuff 18, a measuring gauge 20 and tubing 22. A blood pressure measurement is typically taken by wrapping the pressure cuff 18 around an arm of an individual. Air is then pumped into the pressure cuff 18 to tighten the cuff around the patient's arm. Air is pumped into the pressure cuff 18 through the tubing 22 and pressure control valve 14 by squeezing or compressing the hand pump 10. The thumb screw 16 on the pressure control valve 14 also must be closed for the air pumped by the hand pump 10 to inflate the pressure cuff 18. If the thumb screw 16 is not closed, then air will exit the pressure control valve 14 through the thumb screw 16, rather than pass through the tubing 22 to inflate the pressure cuff 18. Opening the thumb screw 16 will also release any air contained in the pressure cuff 18 or the tubing 22.

With the thumb screw 16 closed, air pumped by the hand pump 10 through the pressure control valve 14 and the tubing 22 causes the pressure cuff 18 to expand and tighten around the patient's arm. The measuring gauge 20 is monitored while more air is continually pumped from the hand pump 10 into the pressure cuff 18 until a pressure level is reached at which blood flow through an artery in the patient's arm is fully occluded. Once this desired starting pressure level is achieved, the thumb screw 16 is slightly opened to allow air from the pressure cuff 18 to be controllably released through the pressure control valve 14 while the doctor or nurse listens with a stethoscope for korotkoff sounds in the patient's artery representing systolic and diastolic blood pressure. The measuring gauge 20 is monitored until both the systolic and the diastolic pressure levels are determined. At that point, the measurement is complete and the thumb screw 16 is completely opened to allow any air remaining within the pressure cuff 18 to be released through the pressure control valve 14.

The hand pump 10 is typically an oval bulb made of black rubber. In a preferred embodiment, the hand pump 10 is created in the likeness of an animal, such as a bear as is shown in FIG. 1. By constructing the hand pump 10 in the likeness of an animal, a child is more likely to associate positively with the hand pump 10 due to a familiarity with its shape. The child's positive association with the hand pump 10 helps avoid anxiety in the child from an unfamiliar device. Anxiety can make it difficult if not impossible, for medical personnel to accurately measure the child's blood pressure and can lead to misdiagnosis.

Figure 2A:
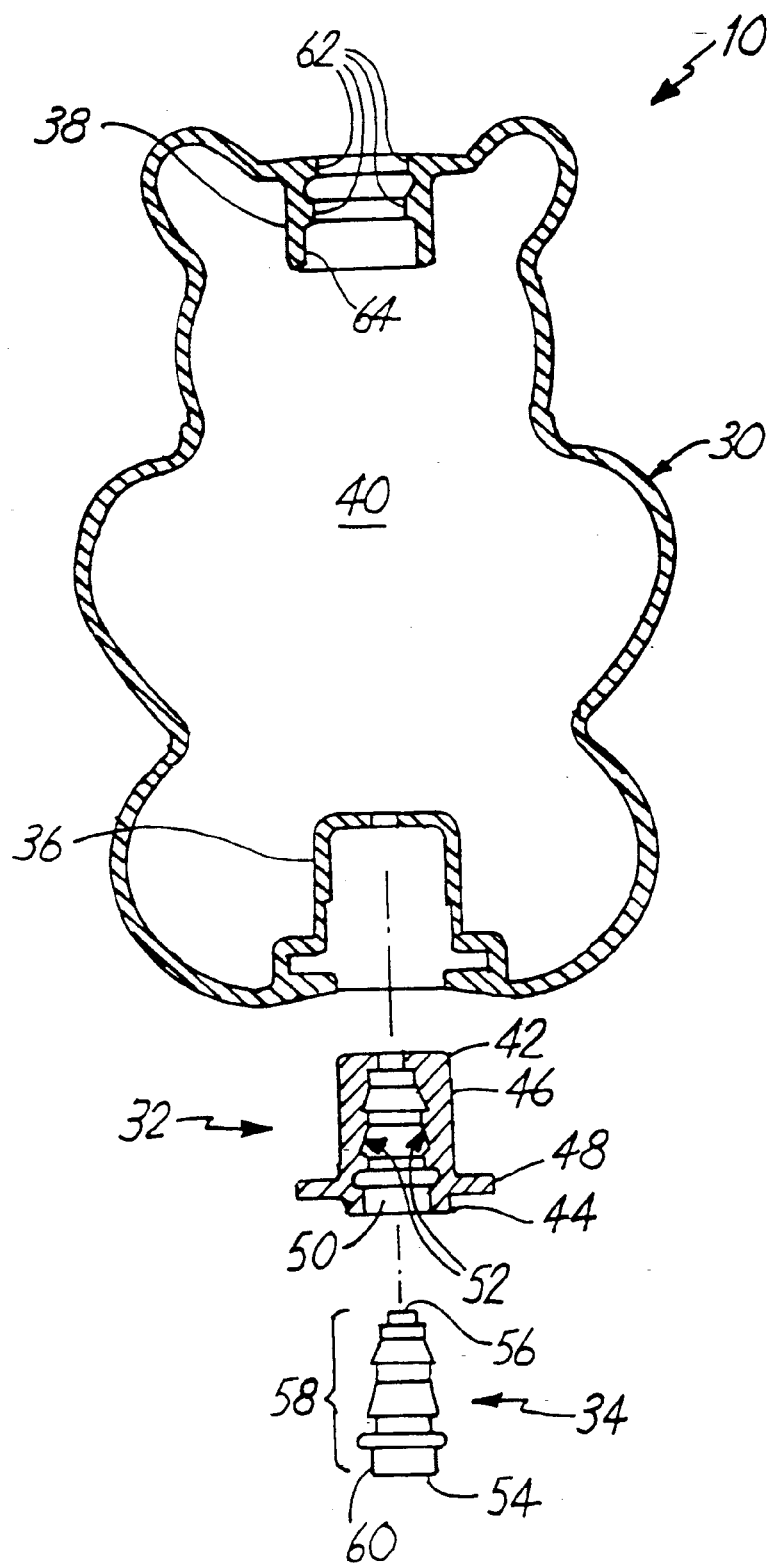
FIG. 2A is an exploded, sectional view of the preferred embodiment of the invention.
Figure 2B:
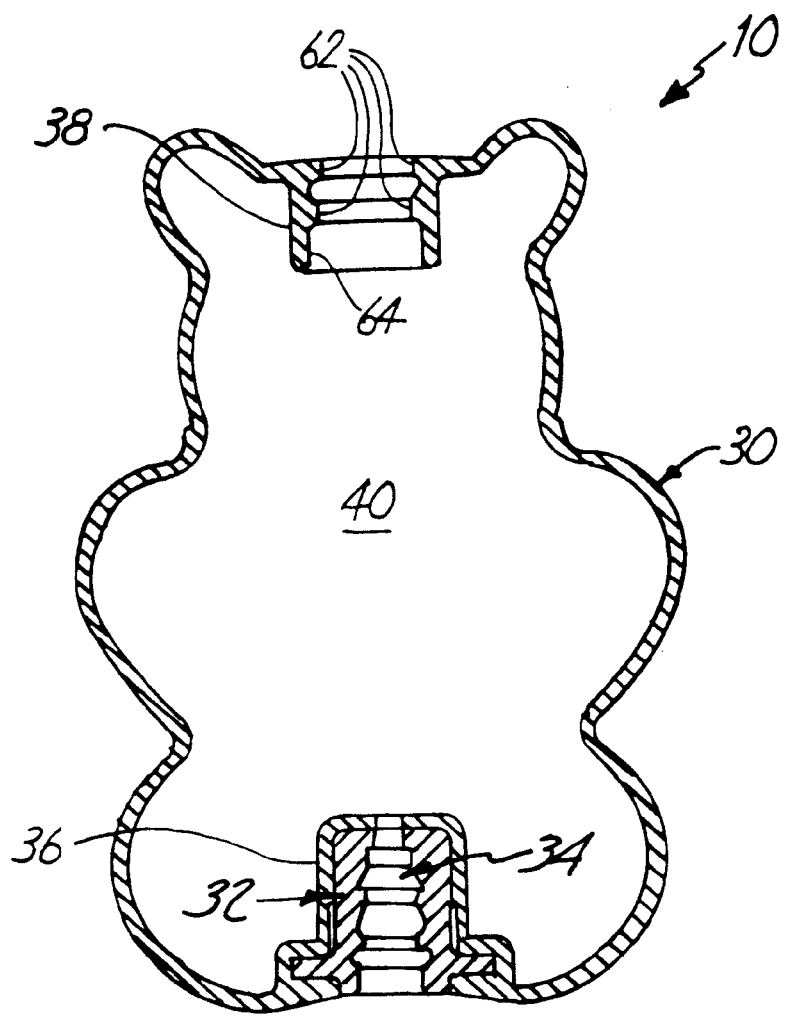
FIG. 2B is an assembled sectional view of the preferred embodiment of the invention.

FIGS. 2A and 2B are sectional views of a preferred embodiment of the hand pump 10. FIG. 2A shows an exploded view of the preferred embodiment while FIG. 2B shows an assembled view of the preferred embodiment. The hand pump 10 includes an inflation bulb 30, a plug 32, and an intake valve 34. The inflation bulb 30 includes an inlet 36 and an outlet 38. The inlet 36 and the outlet 38 are preferably positioned opposite each other along the longest section of the inflation bulb 30. The inflation bulb 30 also creates an inner hollow cavity 40.

The inflation bulb 30 is preferably formed from a non-latex, polymeric material, such as polyvinyl chloride with a plasticizer for achieving a quick response from compressing and releasing the bulb 30. The inflation bulb 30 preferably does not include latex in its material make-up to avoid a potential allergic reaction from either the use or handling of the inflation bulb 30. The bulb 30 preferably has a thickness of approximately 1.50 millimeters. The inflation bulb 30 is preferably approximately 7.80 centimeters long and 5.70 centimeters wide. If the inflation bulb 30 is formed in the shape of an animal, the non-latex, polymeric material used to create the inflation bulb 30 is preferably dyed and painted to match the characteristics of the animal. As illustrated, the hand pump 10 is shaped as a bear so the non-latex, polymeric material is dyed brown and the eyes, nose, feet and bowtie are painted with appropriate colors to match there respective features.

The plug 32 is secured by the inflation bulb 30 at the inlet 36. The plug 32 has a top 42, a bottom 44, and a radial sidewall 46. The sidewall 46 includes an outward radial extension 48. An inner center passage 50 is bore through the plug 32 from the top 42 to the bottom 44. The passage 50 includes a series of notches 52 along its inner surface. The plug 32 is secured at the inlet 36 of the inflation bulb 30 by forming the inflation bulb 30 around the plug 32. The plug 32 is secured to the inflation bulb 30 such that at least a portion of the bottom 44 of the plug 32 is exposed to the surrounding external environment of the hand pump 10. The top 42 of the plug 32 is therefore positioned within the inner hollow cavity 40 of the inflation bulb 30.

Forming the inflation bulb 30 around the plug 32 permanently secures the plug 32 to the inflation bulb 30. In particular, the outward radial extension 48 along the sidewall 46 of the plug 32 maintains the position of the plug 32 at the inlet 36 of the inflation bulb 30. The plug 32 is preferably made of a slightly harder or more rigid non-latex, polymeric material as compared to the inflation bulb 30, such as nylon. In a preferred embodiment, an outer diameter of the radial extension 48 is approximately 19.0 millimeters and a diameter of the sidewall 46 is approximately 11.33 millimeters. Additionally, the plug 32 is preferably placed in a rotational mold for the inflation bulb 30 prior to the inflation bulb 30 being formed. In this manner, the inflation bulb 30 forms integrally around the plug 32 and in particular the radial extension 48 for a permanent connection.

Once the inflation bulb 30 has been molded around the plug 32, the intake valve 34 can be inserted. The intake valve 34 includes an input end 54, an output end 56 and a series of grooves 58 formed along an outer surface 60. The intake valve 34 is secured as part of the hand pump 10 by inserting the output end 56 into the passage 50 at the bottom 44 of the plug 32. Once the intake valve 34 is in place, pressure is applied to the intake valve 34 to insert it into the plug 32. The intake valve 34 should be inserted into the plug 32 so that its input end 54 is secured at the bottom 44 of the plug 32 and its output end 56 is secured at the top 42 of the plug 32. The intake valve 34 is secured and retained within the plug 32 by the series of notches 52 placed along the inner surface of the passage 50 of the plug 32. The series of notches 52 mate with the series of grooves 58 placed along the outer surface 60 of the intake valve 34. The manner in which the grooves 58 and notches 52 mate prevent the intake valve 34 from being removed out of the plug 32.

The intake valve 34 is a pressure differential type of air valve. The intake valve 34 operates by allowing air to flow through the input end 54 and out the output end 56 when a pressure differential exists across the intake valve 34. A pressure differential exists when the pressure within the inner hollow cavity 40, at the output end 56 of the intake valve 34, is less than the pressure of the surrounding external environment at the input end 54. The pressure differential across the intake valve 34 causes a seal within the intake valve 34 to unseat and allow external air to flow through the seal and into the inner hollow cavity 40 of the inflation bulb 30. Air continues to flow through the intake valve 34 until the pressure between the inner hollow cavity 40 and the surrounding external environment is equalized. Once the pressure is equalized, the seal in the intake valve 34 is again seated and air flow in either direction is prevented.

The inflation bulb 30 also includes a series of ribs 62 placed along an inner surface 64 of the outlet 38. The series of ribs 62 secure the inflation bulb 30 to the pressure control valve 14 at the outlet 38. Once the inflation bulb 30 is connected to the pressure control valve 14, the hand pump 10 can function as part of the sphygmomanometer 12.

The hand pump 10 functions as part of the sphygmomanometer 12 by supplying air to inflate the pressure cuff 18. Air is provided from the hand pump 10 by compressing the inflation bulb 30, which causes the air contained within the inner hollow cavity 40 to be forced out through the outlet 38, through the pressure control valve 14 and into the pressure cuff 18 via the tubing 22. The pressure control valve 14, similar to the air intake valve 34, allows air to only flow in one direction when a pressure differential exists, from the hand pump 10 to the tubing 22. The thumb screw 16, however, is included as part of the pressure control valve 14 and can be opened to act as a release valve for air passing through the pressure control valve 14 or contained in either the pressure cuff 18 or the tubing 22. The hand pump 10 works in a repeated cycle to transfer air from within the inner hollow cavity 40 of the inflation bulb 30 to the pressure cuff 18 for inflation.

The manner in which the hand pump is constructed prevents the plug and the intake valve from being removed from the inflation bulb and either being lost or creating a choking hazard. Further, the familiar features of a animal, such as a teddy bear, as the shape of the inflation bulb is inviting to a child and helps them avoid becoming anxious. The hand pump thus assists the medical examiner in conducting the blood pressure test as well as improves the results which otherwise might be skewed and possibly lead to misdiagnosis as a result of the child's anxiety.

Although the present invention has been described with reference to preferred embodiments, workers skilled in the art will recognize that changes may be made in form and detail without departing from the spirit and scope of the invention. For example, the inflation bulb can be formed in the likeness of many different animals or things, such as a dog, a car, or a block. Also, the dimensions, or material used to construct the hand pump, or its components, could also be altered. The invention thus provides a hand pump that can be used as part of a sphygmomanometer that is inviting and safe for use with children.

What is claimed is:

1. A hand pump for connection to a pressure control valve as part of a sphygmomanometer, the hand pump comprising:
    an inflation bulb shaped with the characteristics of an animal having an inlet, an outlet, and an inner hollow cavity, wherein the outlet is connectable to the pressure control valve of the sphygmomanometer;
    a plug fixed within the inner hollow cavity of the inflation bulb at the inlet; and
    an intake valve secured within the plug.

2. The hand pump of claim 1, wherein the plug includes a top, a bottom, an annular sidewall having a radial outward extension, and an inner center passage bore from the top to the bottom, wherein the passage is notched to fit and retain the intake valve therein between the top and the bottom.

3. The hand pump of claim 2, wherein the inflation bulb is formed around and encloses the plug at the inlet, such that an input end of the intake valve at the bottom of the plug is externally exposed and an output end of the inlet valve at the top of the plug empties into the inner hollow cavity of the inflation bulb.

4. The hand pump of claim 1, wherein the outlet includes a series of ribs for connecting the hand pump to the pressure control valve.

5. The hand pump of claim 1, wherein the inflation bulb is molded to the plug.

6. The hand pump of claim 1, wherein the plug is more rigid than the inflation bulb.

7. The hand pump of claim 1, wherein the inflation bulb is made of a non-latex, polymeric material.

8. A hand pump for connection to a pressure control valve as part of a sphygmomanometer, the hand pump comprising:
    a compressible member creating an inner hollow cavity;
    an inlet through the compressible member into the inner cavity;
    a plug having a top, a bottom, an annular sidewall and an inner passage bore from the top to the bottom, the plug secured within the inner cavity of the compressible member at the inlet with an outward radial extension on the annular sidewall;
    an intake valve secured within the inner passage bore of the plug to allow air flow through the intake valve and into the inner cavity when a pressure differential exists across the intake valve such that the pressure within the cavity is less than the pressure external to the compressible member; and
    an outlet through the compressible member and from the inner cavity for connecting the compressible member to the pressure control valve of the sphygmomanometer.

9. The hand pump of claim 8, wherein the passage bore in the plug includes a series of notches which correspond to an outer surface shape of the intake valve to secure the intake valve therein, such that an input end of the intake valve is secured at the bottom of the plug and an output end of the intake valve is secured at the top of the plug.

10. The hand pump of claim 8, wherein the outlet has a series of ribs to secure the pressure control valve therein.

11. The band pump of claim 8, wherein the compressible member has a shape of an animal.

12. The hand pump of claim 8, wherein the compressible member is made of a non-latex, polymeric material.

13. The hand pump of claim 8, wherein the compressible member is molded to the plug.

14. The hand pump of claim 8, wherein the plug is more rigid that the compressible member.

* * * * *

UNITED STATES PATENT AND TRADEMARK OFFICE
CERTIFICATE OF CORRECTION

PATENT NO.     : 6,258,036 B1                                              Page 1 of 1
DATED          : July 10, 2001
INVENTOR(S)    : Daniel G. Cook It is certified that error appears in the above-identified patent and that said Letters Patent is hereby corrected as shown below:

<u>Column 2,</u>
Line 11, delete "band", insert -- hand --

<u>Column 6,</u>
Line 48, delete "band", insert -- hand --

Signed and Sealed this

Second Day of April, 2002

*Attest:*

JAMES E. ROGAN
*Attesting Officer*          *Director of the United States Patent and Trademark Office*